US008084627B2

(12) United States Patent
Koide et al.

(10) Patent No.: US 8,084,627 B2
(45) Date of Patent: Dec. 27, 2011

(54) HYDROXYMETHYL FLUORESCEIN DERIVATIVES FOR USE AS BIOLOGICAL MARKERS AND DYES

(75) Inventors: Kazunori Koide, Pittsburgh, PA (US); Amanda L. Garner, Pittsburgh, PA (US); Fengling Song, Pittsburgh, PA (US)

(73) Assignee: University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 744 days.

(21) Appl. No.: 12/011,529

(22) Filed: Jan. 28, 2008

(65) Prior Publication Data
US 2008/0275257 A1 Nov. 6, 2008

Related U.S. Application Data

(60) Provisional application No. 60/897,574, filed on Jan. 26, 2007.

(51) Int. Cl.
*C07D 311/82* (2006.01)
(52) U.S. Cl. .......................... 549/388; 549/223
(58) Field of Classification Search .................. 549/344, 549/388, 223
See application file for complete search history.

(56) References Cited

U.S. PATENT DOCUMENTS

| 4,490,543 | A | 12/1984 | Bergquist et al. |
| 4,569,932 | A | 2/1986 | Bergquist et al. |
| 5,137,800 | A | 8/1992 | Neckers et al. |
| 5,525,595 | A | 6/1996 | Takagaki et al. |
| 5,639,802 | A | 6/1997 | Neckers et al. |
| 6,043,428 | A | 3/2000 | Han et al. |
| 2005/0059831 | A1 | 3/2005 | Blazecka et al. |
| 2006/0057658 | A1 | 3/2006 | Ying et al. |

FOREIGN PATENT DOCUMENTS

| EP | 1674579 A1 | 6/2006 |
| EP | 1749870 A1 | 2/2007 |
| JP | 05222298 A * | 8/1993 |
| WO | PCT/GB91/01941 | 5/1992 |
| WO | PCT/US02/09066 | 10/2002 |
| WO | PCT/US2005/023947 | 8/2006 |
| WO | PCT/GB2005/004733 | 9/2006 |

OTHER PUBLICATIONS

Krol et. al. "Macroscopic pKa Calculations for Fluorescein and Its Derivatives" Journal of Chemical Theory & Computation 2006, 2, 1520-1529.*
Urano et. al. "Evolution of Fluorescein as a Platform for Finely Tunable Fluorescence Probes" Journal of the American Chemical Society 2005, 127, 4888-4894.*
CAS registry file, Mar. 7, 2001.*
Chemical abstracts Registry No. 325993-71-3 entered on Mar. 7, 2001 from the catalog of OAK Samples Trading, Ltd.*

C.F. Li, et al., Photoluminescence of PMMA doped with fluorescein and carbosilane dendrimer and lasing in PBG resonance cavity, ScienceDirect, Journal of Luminescence vol. 127, pp. 321-326, 2007 Elsevier B.V.
T. Konstantinova, et al., On the Synthesis of Copolymers of Acrylamide with Fluorescent Dyes, Derivatives of 9-Phenylxanthene, Journal of the Univ. Of Chemical Technology and Metallurgy, 41, 2, 2006, pp. 143-146.
V.B. Bojinov, et al., Novel polymerizable light emitting dyes—combination of a hindered amine with 9-Phenylxanthene fluorophore. Synthesis and photophysical investigations, ScienceDirect, Dyes and Pigments, vol. 74, pp. 187-194, 2006 Elsevier Ltd.
N. Merbouh, et al., 3-Mercaptopropanol as a Traceless Linker for Chemical and Enzymatic Synthesis of Oligosaccharides, Organic Letters, vol. 9, No. 4, pp. 651-653, J. Am. Chem. Soc. 2007.
B.A. Sparano, et al., Effect of Binding Conformation on Fluorescence Quenching in New 2',7'-Dichlorofluorescein Derivatives, Organic Letters, vol. 6, No. 12, pp. 1947-1949, J. Am. Chem. Soc. 2004.
D. Yang, et al, A Highly Selective Fluorescent Probe for the Detection and Imaging of Peroxynitrite in Living Cells, vol. 128, pp. 6004-6005, J. Am. Chem. Soc. 2006.
N. C. Ganguly, et al., Mild and efficient deprotection of allyl ethers of phenols and hydroxycoumarins using a palladium of charcoal catalyst and ammonium formate, ScienceDirect, Tetrahedron Letters vol. 47, pp. 5807-5810, 2006 Elsevier Ltd.
J. Mitra, et al., Palladium (II) catalyzed oxidation reactions of coumarin derivatives, vol. 31B, Oct. 1992, pp. 693-695, J. Indian Chem. Soc.
D.R. Buckle, et al., Aryloxyalkyloxy- and Aralkyloxy-4-hydroxy-3-nitrocoumarins Which Inhibit Histamine Release in the Rat and Also Antagonize the Effects of a Slow Reacting Substance of Anaphylaxis, vol. 22, pp. 158-168, J. Am. Chem. Soc. 1979.
K.R. Shah, et al., Studies in the Synthesis of Furocoumarins Part XXI: Synthesis of Furocoumestan derivatives, vol. LII, Mar. 1975, pp. 224-226, J. Indian Chem. Soc.
K.P. Sanghvi, et al., Studies in the Synthesis of Furocoumarins: Part XXIV: Synthesis of Difurocoumarin derivatives, vol. LVI, Jan. 1979, pp. 56-58, J. Indian Chem. Soc.
V.K. Ahluwalia, et al., A Convenient Synthesis of Psoralen Derivatives Oxygenated in the Pyrone Ring: 4-Methoxypsoralen and 3,4-Dimethoxypsoralen (Halkendin), 1979, vol. 32, pp. 1361-1367, Aust. J. Chem.
F. Song, et al., A Highly Sensitive Fluorescent Sensor for Palladium Based on the Allylic Oxidative Insertion Mechanism, vol. 129, pp. 12354-12355, J. Am. Chem. Soc. 2007.
B. Tang, et al., Flow injection kinetic spectrofluorimetric determination of trace amounts of palladium, ScienceDirect, Analytica Chimica Acta, vol. 511, pp. 17-23, 2004 Elsevier B.V.
D.A. Mikaelyan, et al., Extraction-Fluorometric Determination of Platinum(IV) With Rhodamine 6G, pp. 212-213, 1987 Plenum Publishing Corp.

(Continued)

*Primary Examiner* — David K O Dell
(74) *Attorney, Agent, or Firm* — Stephen A. Bent; Foley & Lardner LLP

(57) ABSTRACT

Hydroxymethyl fluorescein derivatives are provided. The derivatives can be easily conjugated to other molecules, and are more permeable than other fluorescein derivatives. Methods of making the derivatives are also provided.

6 Claims, 2 Drawing Sheets

OTHER PUBLICATIONS

I. Hamelers, et al., Carboplatin nanocapsules: a highly cytotoxic, phospholipid-based formulation of carboplatin, pp. 2007-2012, Mol Cancer Ther 2006; 5(8). Aug. 2006.

Y. Urano, et al., Evolution of Fluorescein as a Platform for Finely Tunable Fluorescence Probes, vol. 127, pp. 4888-4894, J. Am. Chem. Soc. 2005.

STN-CAS search results, various abstracts, copyright 2008 ACS on STN.

Vol. 8, No. 4, Jan. 2006, pp. 581-584, American Chemical Society 2006.

* cited by examiner

US 8,084,627 B2

HYDROXYMETHYL FLUORESCEIN DERIVATIVES FOR USE AS BIOLOGICAL MARKERS AND DYES

CROSS-REFERENCE TO RELATED APPLICATION

This application claims priority under 35 U.S.C. 119(e) to Provisional Application Ser. No. 60/897,574, filed Jan. 26, 2007, incorporated by reference in its entirety.

FIELD OF THE INVENTION

This invention relates to fluorescein derivatives with a hydroxymethyl group in lieu of the conventional carboxy group, for use as biological markers and dyes.

BACKGROUND OF THE INVENTION

Fluorescent imaging is becoming an increasingly important technology for examining the real-time localizations of biologically relevant molecules within model organisms such as the zebrafish. Such imaging often requires the use of 2',7'-dichlorofluorescein (DCF, FIG. 1), 2',7'-difluorofluorescein (Oregon Green), or one of their derivatives since each offers pH insensitivity, compact size, and high quantum yield. However, the negatively charged carboxyl groups in these compounds can non-specifically interact with positively charged biomolecules. Furthermore, the carboxyl group is often found to be responsible when inherently cell-permeable molecules become impermeable following conjugation to fluorescein.

The Lindqvist group showed that the carboxyl group of these compounds was not essential for fluorescence emission. This observation was corroborated by the Nagano group at the University of Tokyo, who replaced fluorescein's carboxyl group with a methyl group, forming a compound, Tokyo Green, which demonstrated no loss of quantum yield. A similar methyl substitution was carried out by the Peterson group at The Pennsylvania State University, this time with Oregon Green, to produce Pennsylvania Green. In live human cells, Pennsylvania Green was more fluorescent than Tokyo Green due to its pH-insensitivity. While Pennsylvania Green is an excellent fluorescent probe, the synthesis of its conjugation-amenable derivatives is a lengthy process, requiring 10 linear steps. What is needed are fluorescent probes that are cell permeable and easily synthesized from commercially available materials.

SUMMARY OF THE INVENTION

Accordingly, the present invention provides a scalable and concise synthesis of tissue-permeable DCF derivatives, some of which couple the favorable fluorescent and solubility properties of Pennsylvania Green with a "handle" that is easily conjugated to target biomolecules.

In one aspect, the present invention provides fluorescein derivatives having the formula:

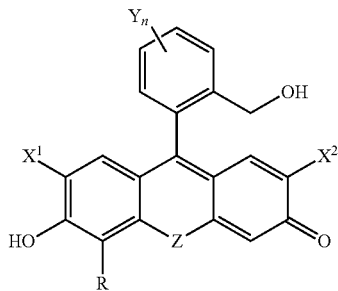

where $X^1$ and $X^2$ are each independently hydrogen or halogen;
Z is O, S, Se, or NR', wherein R' is hydrogen or a substituted or unsubstituted alkyl group of 1-30 carbons, optionally with heteroatoms O, N, or S;
n is an integer from 1 to 4;
Y is selected from hydrogen or a functional group as that term is understood in the art, and each occurrence of Y is independently selected from every other occurrence; and R is hydrogen or a substituted or unsubstituted allyl group of 1-30 carbons and optionally heteroatoms such as oxygen, nitrogen or silicon.

Methods of making the above compounds are also provided. The methods comprise the steps of:
a) adding a protecting group to fluorescein or a fluorescein derivative; b) reducing the carboxy-ester to an alcohol; c) optionally, re-oxidizing the compounds produced in step b with an oxidizing agent; d) selecting a step from the following two options: 1) a Claisen rearrangement, or 2) removing the protecting group from compounds prepared from step (b) or step (c).

BRIEF DESCRIPTION OF THE DRAWINGS

The invention is further illustrated by the following non-limiting drawings in which.

DETAILED DESCRIPTION OF THE INVENTION

Figure 1:
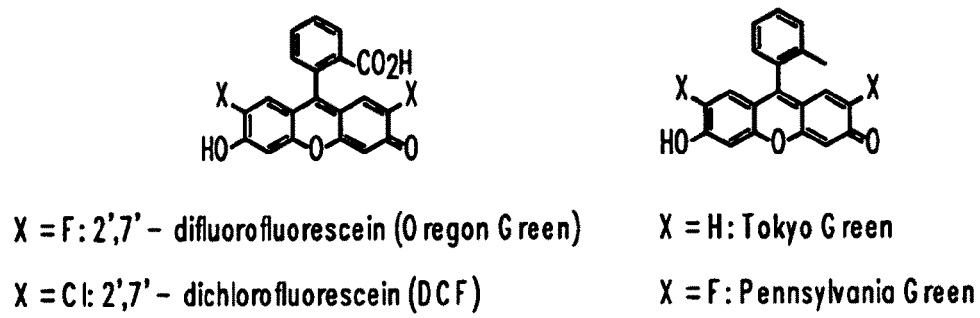
FIG. 1 is a diagram of prior art fluorescein derivatives.

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

In one aspect, the present invention provides fluorescein derivatives having the formula:

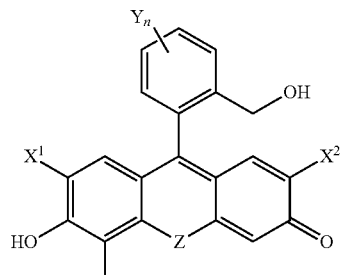

where $X^1$ and $X^2$ are each independently hydrogen or halogen;
Z is O, S, Se, or NR', wherein R' is hydrogen or a substituted or unsubstituted alkyl group of 1-30 carbons, optionally with heteroatoms O, N, or S;
n is an integer from 1 to 4;

Y is selected from hydrogen or a functional group as that term is understood in the art, and each occurrence of Y is independently selected from every other occurrence; and R is hydrogen or a substituted or unsubstituted allyl group of 1-30 carbons and optionally heteroatoms such as oxygen, nitrogen or silicon.

"With heteroatoms" means that one or more carbons in the carbon chain can optionally be replaced with oxygen, nitrogen or silicon atoms.

In some preferred embodiments, Y is hydrogen, R is a substituted or unsubstituted allyl group and $X^1$ and $X^2$ are chlorine. In other preferred embodiments, Y is hydrogen, R is hydrogen and $X^1$ and $X^2$ are chlorine.

The above fluorescein derivatives can be used as markers or dyes, as either of those terms are understood in the art. Fluorescein-based dyes are well known, and the compounds of the present invention can be substituted for other known fluorescein or fluorescein-based compounds or derivatives in dyes and for use as markers.

In certain embodiments, compounds of the present invention are conjugation-ready without further manipulation via the primary hydroxy group as a handle. In other embodiments, compounds of the present invention can be conjugated via olefin-cross metathesis of the allyl group, via linking groups or directly, to biomolecules or other molecules of interest. Conjugation of fluorescein and fluorescein derivatives is well known in the art.

As used herein, the term "conjugate" means covalent attachment of the inventive compound to another molecule, for use as a marker, dye, method of detection, and the like.

Compounds of the invention may be used to prepare a variety of conjugates. In one aspect of the invention, the conjugated substance (substance to which the inventive compound is attached) is a member of a specific binding pair. In another aspect of the invention, the conjugated substance is a molecular carrier. In yet another aspect of the invention, the conjugated substance is a biomolecule that is an amino acid, a peptide, a protein, a nucleoside, a nucleotide, an oligonucleotide, a nucleic acid polymer, or a carbohydrate. In yet another aspect of the invention, the conjugated substance is a polar moiety, or a masked polar moiety. In yet another aspect of the invention, the conjugated substance is a solid or semi-solid matrix.

The conjugated substance also may be a member of a specific binding pair or a molecular carrier. Specific binding pair members typically specifically bind to and are complementary with the complementary member of the specific binding pair. Conjugated members of a specific binding pair typically are used to localize the compound of the invention to the complementary member of that specific binding pair. Some examples of binding pairs include, but are not limited to, antibody-antigen; avidin (streptavidin)-biotin; DNA-aDNA; enzyme-enzyme substrate; lectin-carbohydrate; receptor-ligand; and RNA-aRNA binding pairs, including complementary nucleic acid bindings and host-guest interactions.

Where the conjugated substance is a carrier, it typically is a biological or artificial polymer. Biological polymers include proteins, carbohydrates, and nucleic acid. Artificial polymers include polyethylene glycols and polymeric microparticles composed of polystyrene, latex, or other polymeric material. A conjugated carrier is a carbohydrate that is a dextran, or amino-substituted dextran, or a polymeric microparticle. Such carriers are useful for altering the solubility of the compound, enhancing its retention within cell membranes, or decreasing its compartmentalization within cells.

Where the conjugated substance is a polar moiety, the conjugated substance is typically substituted one or more times by a highly polar functional group, such as a carboxylic acid or sulfonic acid. To improve loading into cells, the polar moiety typically is masked or protected, temporarily rendering it more lipophilic and therefore more cell-permeant. One such masking group is an ester group that is cleaved by esterases to release the free polar moiety within cell membranes, where they are well-retained. Typically, the polar moiety is a carboxylic acid, a dicarboxylic acid, or a tricarboxylic acid moiety that is protected as an ester, typically as an acetoxymethyl ester.

Where the conjugated substance is a solid or semi-solid matrix, the conjugated substance may be a metal or glass surface, and may be, for example, the sides or bottom of a microwell, or a slide, or the surface of a chip. The compound of the invention is optionally covalently bound to a fiber optic probe, where the probe is composed of glass or functionalized glass (e.g., aminopropyl glass), or the compound is attached to the fiber optic probe via an intermediate polymer, such as polyacrylamide.

The conjugated substance may be directly attached to a compound of the present invention, or it may be attached via a linker or spacer. A linker provides additional functionality and options for attaching the fluorescent compounds of the present invention to different types of molecules. A spacer such as a two to seven methylene carbon chain can prevent the compound from interfering with the biological activity of the conjugated substance. Both linkers and spacers for attaching fluorescein compounds to biomolecules and other molecules of interest are well known in the art. See, for example, U.S. Pat. Nos. 6,811,979; 5,468,854; and 7,160,735, each completely incorporated herein by reference.

For example, the fluorescein may be assembled having an appropriate functionality at one end for linking to polypeptide-binding moieties. A variety of functionalities can be employed. Thus, the functionalities normally present in a peptide, such as carboxy, amino, hydroxy and thiol may be the targets of a reactive functionality for forming a covalent bond. The fluorescein marker is linked in accordance with the chemistry of the linking group and the availability of functionalities on the polypeptide-binding moiety. For example, antibodies and fragments thereof such as Fab' fragments, specific for a polypeptide, a thiol group will be available for using an active olefin, e.g., maleimide, for thioether formation. Where lysines are available, one may use activated esters capable of reacting in water, such as nitrophenyl esters or pentafluorophenyl esters, or mixed anhydrides as with carbodiimide and half-ester carbonic acid. There is ample chemistry for conjugation in the literature, so that for each specific situation, there is ample precedent in the literature for the conjugation.

Thus, as used herein, the term "linker" is defined to mean a molecule that is attached to the compounds of the present invention, to provide the additional desired functionality for further attachment to a molecule of interest.

Thus, in an additional aspect, compounds of the present invention are conjugated with biomolecules. In some preferred embodiments, the biomolecule is a naturally occurring or synthetically modified amino acid, peptide, protein, nucleoside, nucleotide, oligonucleotide, nucleic acid polymer, or carbohydrate. In other preferred embodiments, the biomolecule is one member of a binding pair.

In additional aspects, the present invention provides methods of making fluorescein derivatives of the formula

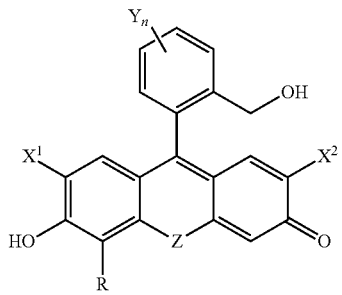

where $X^1$ and $X^2$ are each independently hydrogen or halogen;

Z is O, S, Se, or NR', wherein R' is hydrogen or a substituted or unsubstituted alkyl group of 1-30 carbons, optionally with heteroatoms O, N, or S;

n is an integer from 1 to 4;

Y is selected from hydrogen, or a functional group as that term is understood in the art, and each occurrence of Y is independently selected from every other occurrence; and R is hydrogen or a substituted or unsubstituted allyl group of 1-30 carbons and optionally heteroatoms such as oxygen, nitrogen or silicon. The method comprises the steps of:

a) adding a protecting group to fluorescein or a fluorescein derivative; b) reducing the carboxy-ester to an alcohol; c) optionally, re-oxidizing the compounds produced in step b with an oxidizing agent; d) selecting a step from the following two options: 1) a Claisen rearrangement, or 2) removing the protecting group from compounds prepared from step (b) or step (c).

"Alkyl group" means including linear or branched carbon groups, substituted or unsubstituted, preferably 1-30 carbons in length, more preferably 1-20 carbons, and even more preferably, between 1 and 8 or 1 and 6 carbons.

It will be understood that the terms "substitution" and "substituted with" are art-recognized and include the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Where R is hydrogen, the protecting group can be any suitable hydroxyl-protecting group. The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., Protective Groups in Organic Synthesis 2.sup.nd ed., Wiley, N.Y., (1991). The phrase "hydroxyl-protecting group" is art-recognized and includes those groups intended to protect a hydroxyl group against undesirable reactions during synthetic procedures and includes, for example, benzyl or other suitable esters or ethers groups known in the art.

Where R is an substituted or unsubstituted allylic group, the protecting group is a substituted or unsubstituted allylic group. The Claisen rearrangement is carried out at temperatures between about 1000-200° C., more preferably about 1400-160° C.

The synthesis is carried out in a suitable organic solvent. Suitable reducing agents include, but are not limited to, diisobutylaluminum hydride. Suitable oxidizing agents include, but are not limited to, 2,3-dichloro-5,6-dicyano-1,4-benzoquinone.

When R is hydrogen, the protecting group can be removed by the addition of catalyst or acid. Suitable catalysts include platinum-group metal catalysts, such as palladium or platinum. When a palladium or platinum catalyst is used, the reaction requires the presence of a nucleophile such as morpholine, and also preferably in the presence of a reducing agent such as $NaBH_4$. The protecting group can also be removed by the addition of acid.

EXAMPLES

The invention is further illustrated by the following non-limiting examples.

Example 1

Preparation of Allyl Intermediate

To a solution of bis-O-allyl 2',7'-dichlorofluorescein (about 5.62 g, 11.7 mmol) in $CH_2Cl_2$ at −78° C. under a nitrogen atmosphere was added diisobutylaluminum hydride (about 1.0 M in hexanes, 42.1 mL, 42.1 mmol). The reaction mixture was warmed to about 0° C. for about 1.5 h, and then quenched with saturated $NH_4Cl$ (about 12.6 mL). $Et_2O$ (about 58.5 mL) was added to the solution at 0° C. followed by 2,3-dichloro-5,6-dicyano-1,4-benzoquinone (2.00 g, 8.81 mmol). The resulting solution was allowed to stir for about 15 min at 0° C. The mixture was filtered through a pad of Celite, eluting with $Et_2O$ and concentrated in vacuo. The crude residue was purified by recrystallization from EtOAc and hexanes to afford the allyl intermediate as an orange solid (about 4.4 g, 88%).

Example 2

Preparation of Compound 4 (Pittsburgh Green)

To a solution of the allyl intermediate (about 1.10 g, 2.58 mmol), morpholine (about 225 µL, 2.58 mmol), and sodium borohydride (about 108 mg, 2.84 mmol) in THF (about 32.0 mL) at room temperature was added tetrakis(triphenylphosphine)palladium(0) (about 22.5 mg, 0.019 mmol). The resulting mixture immediately turned from clear to a dark pink color. The solution was allowed to stir for about 1 h, and then quenched with 3N HCl (about 5.0 mL). The resulting two layers were separated and the aqueous layer was extracted with EtOAc (3×50 mL). The combined organic layers were washed with brine (3×50 mL), dried over anhydrous $Na_2SO_4$, and concentrated in vacuo. The crude residue was purified by recrystallization from EtOAc and hexanes to afford Compound 4 as an orange solid (about 973 mg, 97%).

Example 3

Preparation of Compound 3 (Pittsburgh Yellow)

A solution of compound 2 (about 1.00 g, 2.34 mmol) in diphenyl ether (about 5.85 mL) was heated in an oil bath at about 150° C. for about 1.5 h. The solution was then allowed to cool to room temperature and transferred directly to a silica gel column for purification. The column chromatography was performed with 5→20% EtOAc in hexanes to afford compound 3 as a red-orange solid (about 531 mg, 53%).

Example 4

Measurement of Fluorescence

The quantum yields of Compounds 3 and 4 were measured using fluorescein as a standard sample. In a pH 7 phosphate buffer, the quantum yields of these compounds, $\Phi_3$ and $\Phi_4$ were found to be about 0.52 and about 0.80, respectively. These results demonstrate that compounds of the present invention have fluorescent characteristics that are comparable to other DCF derivatives. The emission maxima of 3 and 4 were determined to be about 535 and about 523 nm, respectively. Based on these emission spectra, compounds 3 and 4 were named Pittsburgh Yellow and Pittsburgh Green, respectively.

Example 5

Cell Localization and Permeability Studies

Figure 2:
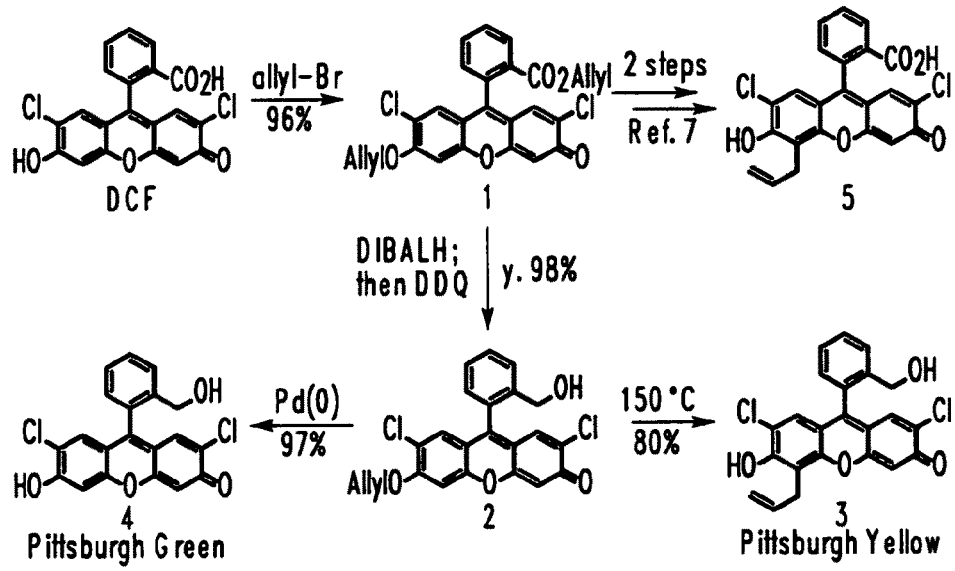
FIG. 2 is a schematic diagram of an embodiment of a synthetic method of the present invention.
Figure 3:
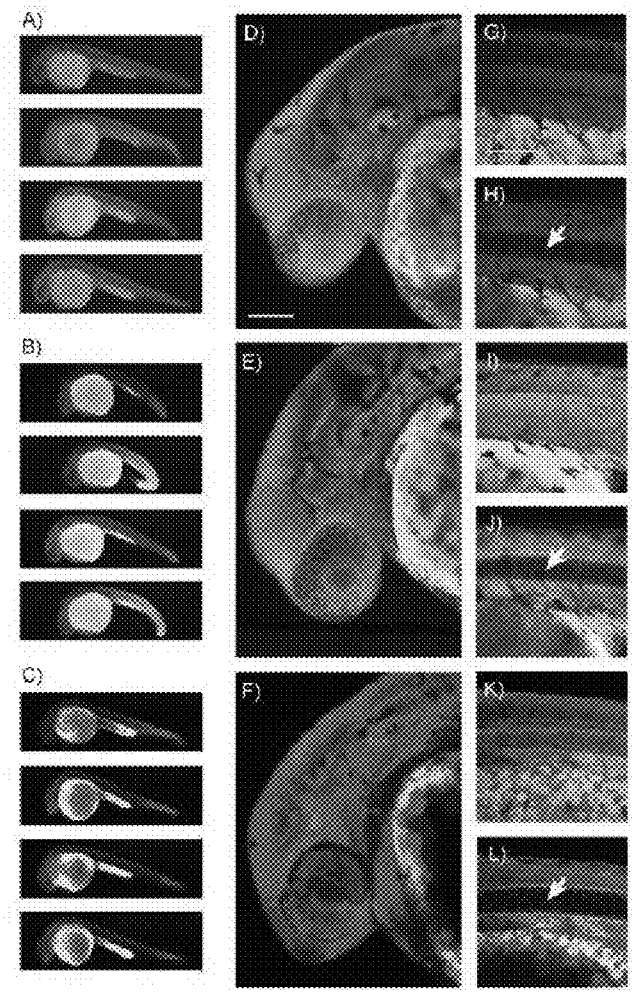
FIG. 3 shows pseudocolored images of 24 h-old zebrafish embryos stained for 1 h with 25 μM Pittsburgh Green (A, D, G, H), Pittsburgh Yellow (B, E, I, J), or BODIPY TR Methyl Ester (C, F, K, L) as follows:
A-C: Representative examples of embryo staining.
D-F: 80 μm confocal Z projections of the head region with otoliths indicated by arrows.
G, I, K: 80 μm Z projections of the tail region (anterior to the left). H, J, L: 1 μm slices from the tail projections. Scale bars=100 μm.

Zebrafish embryos were stained with compound 3 and compound 4 in order to assess the localization and tissue permeability of each compound in vivo. This procedure had not previously been attempted in zebrafish embryos with an unconjugated fluorescein derivative. Therefore, the commercially available BODIPY TR methyl ester was used as a control stain since it has been successfully used for this purpose.[10] Incubation of zebrafish embryos with about 25 µM Pittsburgh Green or Pittsburgh Yellow for about 1 h yielded relatively consistent vital staining (FIG. 2A-B), comparable to the BODIPY control (FIG. 3C). Yolk sacs and yolk extensions always appeared brighter than the embryos themselves (FIG. 3A-C). This is likely the result of compound accumulation within the lipidic yolk platelets that comprise almost the entire volume of the yolk.[11] Embryo viability was not significantly decreased by exposure to any of the staining solutions when compared to carrier (n=60 per compound, p=0.81). However, a slight developmental abnormality in the embryos exposed to 25 µM was detected with Pittsburgh Yellow, including narrowing of the yolk extension and ventral curling of the tail (FIG. 3B). Further toxicity studies showed that neither compounds were toxic at lower concentrations (see below).

Confocal projections of the head (FIG. 3D-F) and tail (FIG. 3G, I, K) spanning 80 µm of the embryonic interior revealed that Pittsburgh Yellow, Pittsburgh Green, and BODIPY TR methyl ester permeate live tissue to similar extents. Structures containing little organic material, including scales and calcified otoliths, were not stained. Confocal sections of the dorsal midline (FIG. 3H, J, L) indicate that the notochord sheath and surrounding tissue are efficiently labeled, while the notochord vacuoles remain unstained. These data support the tissue-specific permeability and localization of the Pittsburgh compounds in vivo. It is noteworthy that Pittsburgh Yellow and Green are more water soluble than BODIPY TR methyl ester.

Toxicity studies were performed to determine the effects of the compounds on zebrafish embryos, by treating embryos from about 3.5 hours post fertilization (hpf) to 48 hpf. Pittsburgh Green exhibited a significant effect on embryo viability at 25 µM (p<0.001), but not at about 8 µM. Pittsburgh Yellow was slightly more toxic, affecting viability at 8 µM (p<0.001), but not at 2.5 µM. These data are consistent with the developmental irregularities observed in the staining experiments.

Example 5

Figure 4:
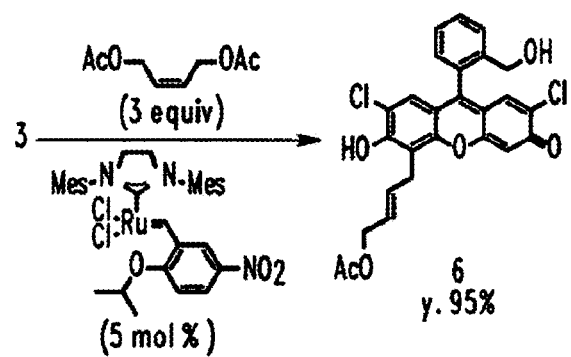
FIG. 4 is a schematic diagram of a method conjugating compounds of the present invention to other molecules.

With these promising results with Pittsburgh Green and Pittsburgh Yellow, it was thought that these compounds and their derivatives would be useful tools in bioimaging. For example, the hydroxy group of compound 2 should be amenable to conjugations because this group can be used as a nucleophile in ether and ester formations and as a leaving group under Mitsunobu conditions. Compound 3 is also conjugation-ready. This principle was demonstrated using olefin cross metathesis. The olefin cross-metathesis between compound 3 and cis-2-butene-1,4-diol diacetate was initially unsuccessful with the widely-used Grubbs II catalyst.[12] However, this coupling was highly efficient with the nitrated Hoveyda-Grubbs catalyst (about 5 mol %) developed by the Grela group,[13] generating acetate 6 in about 95% yield (FIG. 4). Because of high functional group compatibility for olefin cross-metathesis,[14] other functional groups such as maleimide with an appropriate linker could also be introduced to Pittsburgh Yellow.

The present invention provides new fluorescein derivatives that are more synthetically accessible than Tokyo Green and Pennsylvania Green derivatives. Most steps are scalable, indicating potential for manufacturing. Pittsburgh Green and Pittsburgh Yellow exhibited desirable staining and permeability properties with zebrafish embryos. Since these new fluorescein derivatives are more soluble in both water and organic solvents than DCF, these compounds should facilitate chemical syntheses and biological studies of related compounds.

Whereas particular embodiments of this invention have been described above for purposes of illustration, it will be evident to those skilled in the art that numerous variations of the details of the present invention may be made without departing from the invention as defined in the appended claims.

What is claimed is:

1. A Fluorescein derivative having the formula comprising:

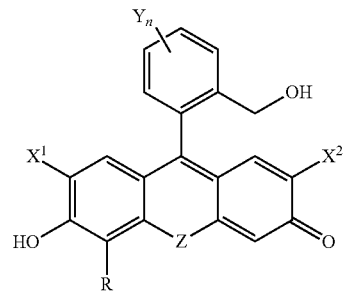

where $X^1$ and $X^2$ are each chlorine;

Z is O; and wherein n=1, Y is hydrogen, R is a hydrogen or substituted or unsubstituted allyl group.

2. A fluorescein derivative of claim 1, wherein n=1, Y is hydrogen, and R is hydrogen.

3. A marker or dye comprising a fluorescein derivative of claim 1.

4. A method of making compounds of the formula:

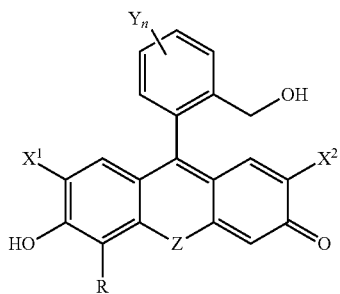

where $X^1$ and $X^2$ are each chlorine;
Z is O;
n is 1;
Y is selected from hydrogen, and R is hydrogen or a substituted or unsubstituted allyl group,
the method comprising the steps of:
a) adding a protecting group to dichlorofluorescein;
b) reducing the carboxy-ester to an alcohol;
(c) selecting a step from the group consisting of 1) a Claisen rearrangement, or 2) removing the protecting group from compounds prepared from step (b).

5. The method of claim 4, wherein R is a substituted or unsubstituted allyl group and in step (c) the step selected is heating the compounds to effect a Claisen rearrangement.

6. The method of claim 4, wherein in (c) the step selected is removing the protecting groups by the addition of catalyst or acid.

* * * * *